United States Patent [19]

Plungis et al.

[11] Patent Number: 4,616,503

[45] Date of Patent: Oct. 14, 1986

[54] TIMER TRIGGER FOR CAPILLARY TUBE VISCOMETER AND METHOD OF MEASURING OIL PROPERTIES

[75] Inventors: Donald W. Plungis, No. Brunswick; Charles S. Seymour, Neptune; William Higgins, Old Budge, all of N.J.

[73] Assignee: Analysts, Inc., Rolling Hills Estates, Calif.

[21] Appl. No.: 714,727

[22] Filed: Mar. 22, 1985

[51] Int. Cl.[4] .......................................... G01N 11/04
[52] U.S. Cl. ............................................ 73/55; 73/54
[58] Field of Search ...................... 73/55, 54; 250/577

[56] References Cited

U.S. PATENT DOCUMENTS

| 3,071,961 | 1/1963 | Heigl et al. | 73/55 |
|---|---|---|---|
| 3,604,247 | 9/1971 | Gramin | 73/55 |
| 3,713,328 | 1/1973 | Aritomi | 73/55 |
| 3,895,513 | 7/1975 | Richardson | 73/55 |
| 3,908,441 | 9/1975 | Virloget | 73/55 |
| 4,366,384 | 12/1982 | Jensen | 250/577 |
| 4,441,358 | 4/1984 | Osborne | 73/55 |

FOREIGN PATENT DOCUMENTS

| 1576163 | 6/1969 | France | 73/55 |
|---|---|---|---|
| 628435 | 2/1982 | Switzerland | 73/55 |

OTHER PUBLICATIONS

Libeyre et al., Automatized Photogoniodiffusometer and Coupling with Automatized Viscosimeter, Polymer Bulletin (1981).
Metz, Viscosity Measurement of Opaque Fluids, IBM, 1976.
Priel et al., Method for Determining the Time of Flow in a Capillary Viscometer, Review of Scientific Instruments, 1972.

Primary Examiner—Stewart J. Levy
Assistant Examiner—Hezron E. Williams
Attorney, Agent, or Firm—Harlan P. Huebner

[57] ABSTRACT

The present invention relates to an improvement in a capillary tube viscometer which includes light sensitive triggering means for timing the flow of oil between two points therein. The improvement includes optic fibers that are positioned on the tube at selected places. In addition, the tube includes impulse receiving means wherein the voltage received from start and stop positions are passed to triggering means and measuring means to translate the same into figures for manual or automatic calculation of time for the flow of oil.

5 Claims, 8 Drawing Figures

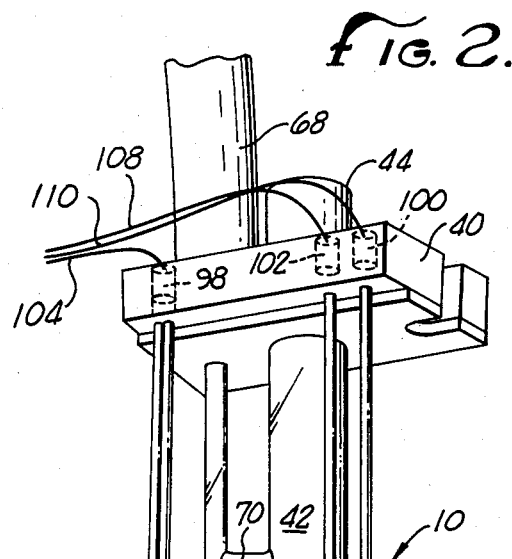
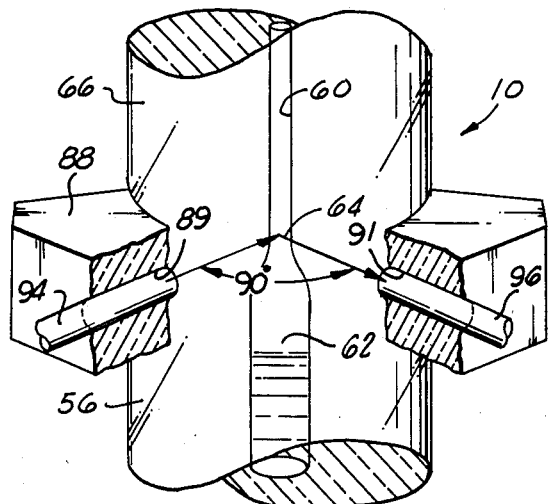
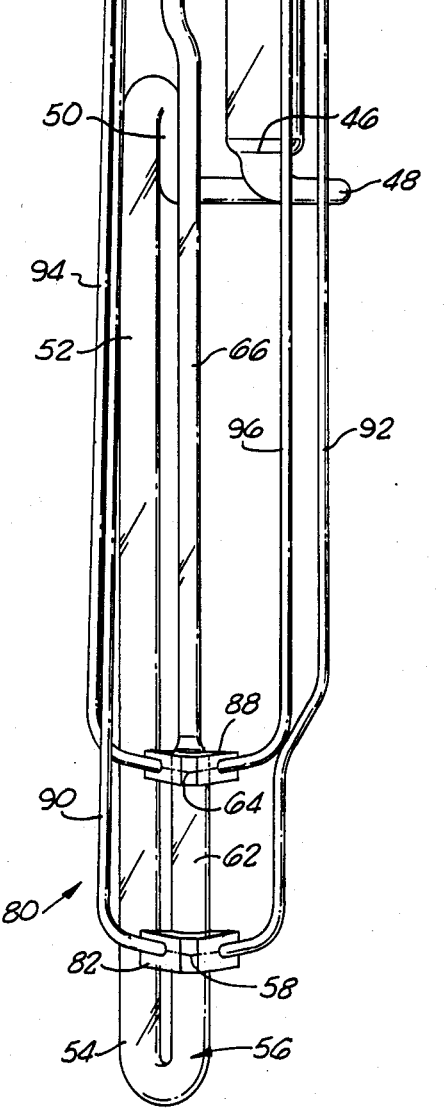
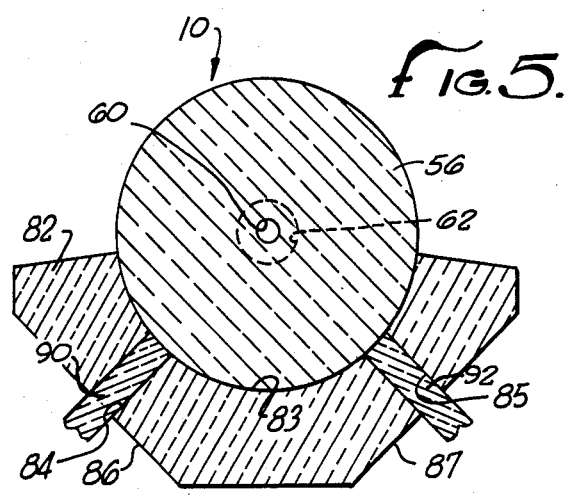

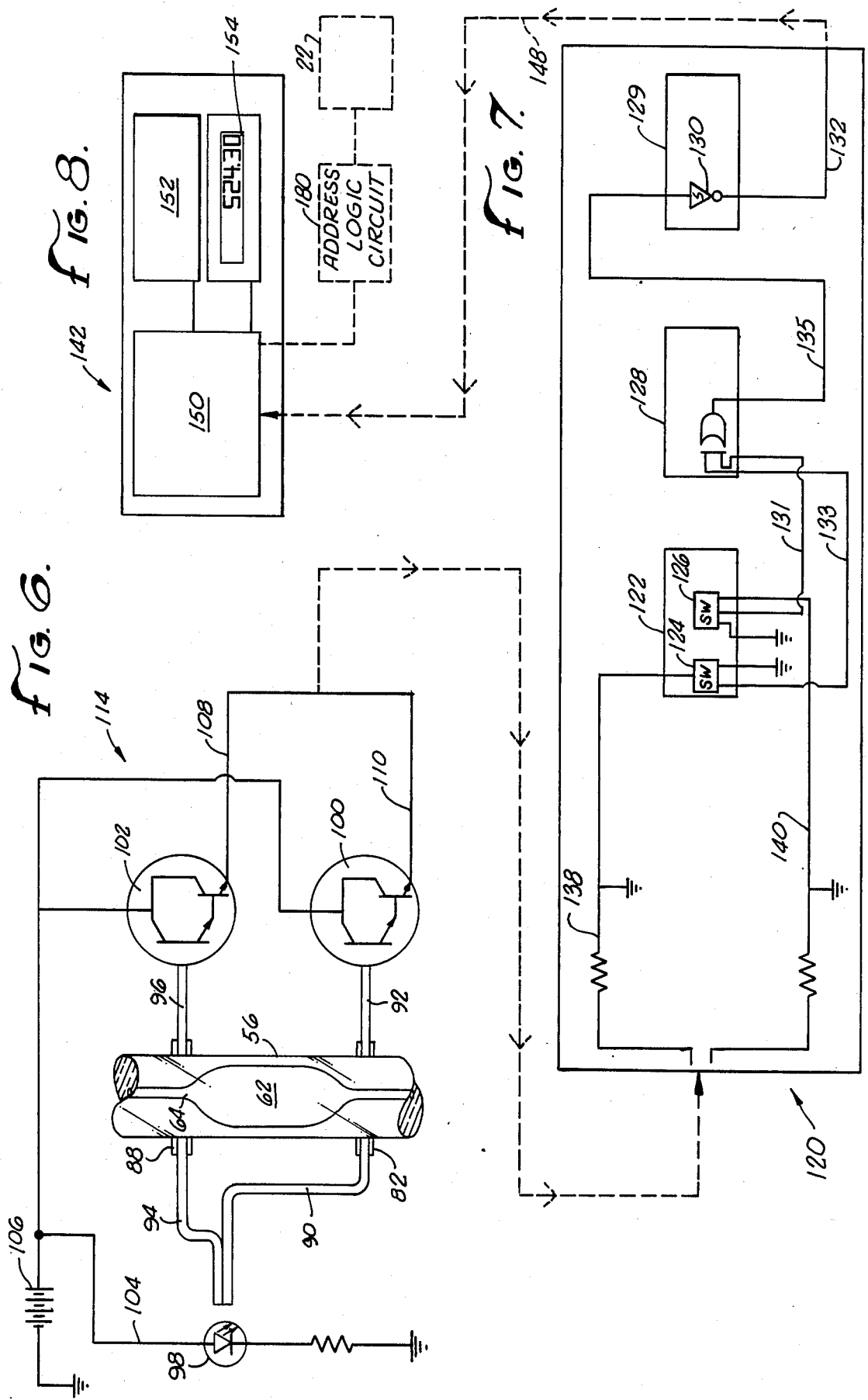

TIMER TRIGGER FOR CAPILLARY TUBE VISCOMETER AND METHOD OF MEASURING OIL PROPERTIES

BACKGROUND OF THE INVENTION

In the testing of liquids and particularly engine oils it is important to determine the viscosity of the oils to assure proper lubrication of an engine. If the engine oil is too thick or too thin proper lubrication of the engine cannot be assured. In some cases oil which has been used in an engine is removed or part thereof for appropriate testing to determine the viscosity. In other cases a customer may desire to know the quality (viscosity) of new oil he is buying in large volume. This is particularly true where there are large fleets of vehicles and oil is bought in large drums for use in the engines of the fleet of vehicles.

There have been many attempts to test the viscosity of motor oil and one in particular that has been used is known as a capillary tube viscometer. This is generally an elongated glass tube with various bends and in certain cases visual marks therein so that as the oil passes between one mark to the other the time it takes may be measured and from that certain charts and tables can be used to calibrate the viscosity of the oil.

There are disadvantages to the visually read capillary viscometer. With concentration, the very best possible visual reading would probably be accurate to within +0.05 seconds. In actuality when several tubes are run simultaneously by an experienced technician, a visually timed accuracy on the order of +0.1 seconds would be expected.

It is desirable that the test for viscosity of the oil should be run at temperatures up to 210° F. This requires that the capillary tube be emersed in a hot oil bath. Therefore the visual inspection which must take place through the heated fluid or liquid within which the capillary tube is emersed can be distorted and confuse readings in multiple tube installations. A true reading is somewhat difficult to achieve.

With fiber optics as described in this invention it is possible to accurately and automatically read and time the start and stop of oil running pass certain points in a capillary tube viscometer.

SUMMARY OF THE INVENTION

It is the purpose of this invention to provide a capillary tube viscometer utilizing fiber optics which will automatically trigger the start and stop of a clock or timing device while a measured quality of oil flows through a capillary tube. The measurement of the time will be extremely accurate to within plus or minus a few hundredths of a second.

Another object of the invention is to provide a capillary tube viscometer system wherein several such viscometers may be simultaneously used for measuring different oils.

It is also a further object of this invention to provide a capillary tube viscometer whereby the measurement of the lapsed time the oil passes on a run may be visually observed and the necessary end figures manually calculated. With a battery of viscometers the measurements may be introduced into a computer and the readings can be automatically taken from the start and stop point and a final computer printout be made available as to the testing directed to the viscosity of the oil.

The present invention may be used on clear or opaque oils because of the principal of the index of reflection and internal reflection. Another object of the present invention is to include a light source which is introduced into the capillary tube by means of fiber optic light guides at one point on the tube and at another point 90° from the entry of the light another fiber optic rod is positioned to pick-up the light. This is true when air is present in the capillary. This is known as the angle of internal reflection. However, with oil present in the tube the angle of reflection is increased to a value greater than 90° due to the higher index of refraction of the oil. Thus when oil passes this point the index of refraction will change and the light will miss the pick-up point or pick-up sensor and the circuit in effect will open. In this way the start time of the flow of oil can be recorded.

The same process is repeated for the stop portion of the oil as it travels through the metered section of the capillary tube. Again light will be introduced through a fiber optic light guide on to the capillary wall and reflected to a sensor spaced 90° from the light guide. As long as there is no oil therein the circuit is closed at the pick-up sensor. However, when the oil passes through the premarked position the angle of reflection becomes greater than 90°. The light is deflected and the circuit in effect will open to send a signal that the oil has passed the stop point.

Another object of the invention is to provide a capillary tube viscometer wherein connections to the tube for the measurements of the travel of oil are collars or fittings whereby there is no clamped or metalic substances to attach the same to the tube whereby there might be a visual obstruction of the tube as the test is being conducted.

While it is not necessary with the present invention that the stop and start points of the oil run be visually observed it is important that inspection can be conducted to determine that there is no foreign matter or any other undesirable function of the tube such as bubbles, etc. as the oil passes through the capillary tube testing area.

A further object of the invention is to provide a glass capillary tube viscometer which may be emersed in relatively hot fluid on the nature of 210° F. whereby the testing portion of the viscometer where the fiber optics are secured to the viscometer will not deteriorate or be affected by the exterior relatively hot medium in which the tests are conducted.

A still further object of the invention is to provide a glass capillary tube viscometer which may be used for measuring either opaque or clear liquids.

These and other objects and advantages will become apparent from the following part of the specification wherein details have been described for the competence of disclosure, without intending to limit the scope of the invention which is set forth in the appended claims.

BRIEF DESCRIPTION OF THE DRAWINGS

These advantages may be more clearly understood from the following detailed description and by reference to the drawings in which:

FIG. 2, is a side elevational view of the glass capillary tube viscometer of this invention;

FIG. 3, is an enlarged sectional view of the upper or stop portion of the capillary tube wherein the oil is measured at the end of its run;

FIG. 4, is an enlarged sectional view of the capillary tube at the start of the run of the oil with it progressing through the capillary tube;

FIG. 5, is a cross sectional view taken of line 5—5 of FIG. 3;

FIG. 6, is a schematic representation of the light source and sensing circuit;

FIG. 7, is a schematic drawing of one form of logic circuitry used to obtain timing of the oil travel as it passes from the start to the stop position in one capillary tube viscometer; and FIG. 8, is a diagrammatic counter memory circuit.

DETAILED DESCRIPTION OF THE PREFERRED EMBODIMENT

Figure 1:
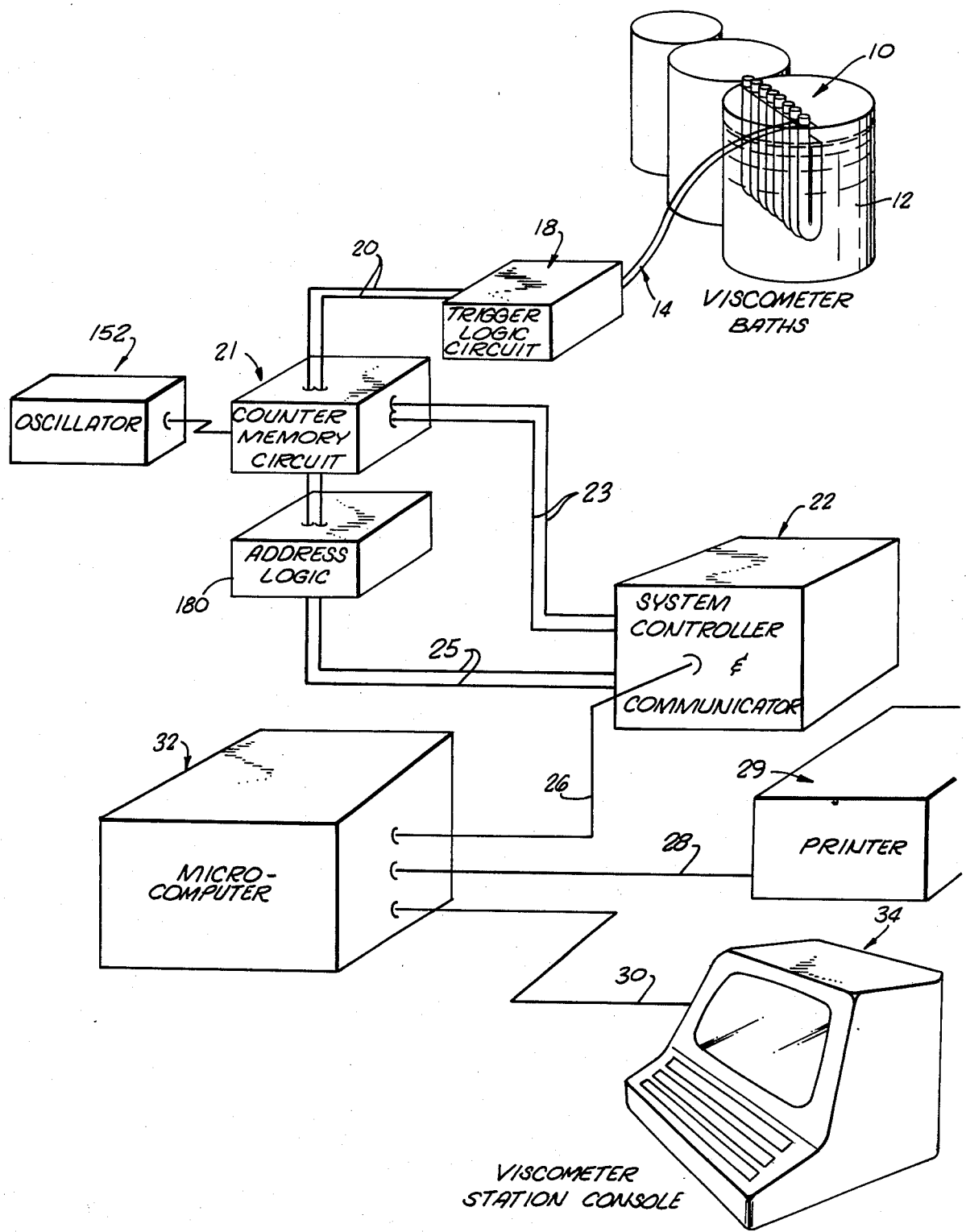
FIG. 1, is a schematic representation of a possible system or method whereby multiple glass capillary tube viscometers may be used for testing different samples of oil.

In FIG. 1 there is illustrated a plurality of glass capillary tube viscometers generally designated 10, as they are in position for testing of different oils in each one of the viscometers 10. It is desirable that appropriate equipment be utilized with each individual viscometer so that computations may be made and readouts rendered.

While FIG. 1 shows the use of a system for reading a multiple number of viscometers 10, it should be realized that a single viscometer 10 may be read through simple trigger circuitry and counter memory circuit, and the readings taken from the stop and start of the oil flow and then appropriate calculations made to arrive at the proper SUS (Sablot Universal Seconds—a unit of viscosity) or other reading value that is to be used in the test.

Again as can be seen from FIG. 1 the viscometers 10 are each mounted within a container 12 into which oil or other fluid is poured so that the oil to be tested in the viscometers 10 are raised to close to 210° F. or desired test temperature so that the test of the oil for its viscosity and possibly other properties can be conducted under engine use conditions.

Lines generally designated 14 object from each of the viscometers 10 to a trigger logic circuit designated 18. From the trigger logic circuit 18, lines 20 (depending on the number of viscometers 10 that are within the container 12 for testing) pass to a counter memory circuit 21.

The system controller/communicator designated 22 address counter locations through lines designated 25 and the address logic 180. Binary data is read through lines generally designated 23. The system controller/communicator 22 controls the sequence in which data from each counter is handled, checked and communicated. At this point raw data could be communicated to a conventional printer.

When considering more than a few viscometer tubes 10 a more elaborate computerization would be the best way to process, manage and store data. Raw data is communicated to a micro computer designated 32 via line generally designated 26. Here conversions are made into actual viscosity units, and data is organized and stored. Data is outputed to a printer 29 or other peripheral device via line generally designated 28. The system console designated 34 is used to input instructions organize samples to designated viscometer locations standardize viscometers, review data, and check tube status (in use or ready). In this way the full system is tied together.

Turning now to FIG. 2, there is illustrated in detail the glass capillary tube viscometer generally designated 10. The viscometer 10 includes a mounting block 40 which includes a plurality of bores therethrough to receive certain portions of the viscometer. The viscometer 10 includes an enlarged upper circular tube portion or reservoir 42 with an open top 44. The reservoir 42 as can be seen at its bottom 46 is reduced and bent to form a restrictive horizontal tube portion 48 having an interior bore of less width than the bore in the upper circular tube portion 42. The horizontal portion 48 is then bent upwardly forming an upper extension 50 and then it is bent upon itself forming a vertical elongated middle tube section 52. At the bottom 54 of the section 52 the tube is bent upwardly forming a vertical upwardly extending tube portion 56. The upper extension 50, middle tube section 52 and upwardly tube portion 56 all have the same common interior bore or diameter. At start point 58 of the upwardly extending portion 56 the tubular bore 60 flairs outwardly to form a bulb 62 to a restrictive stop point 64 where again it becomes restricted. The bore 60 will continue upwardly in upwardly extending end section 66 of the viscometer 10. The upwardly extending end section 66 projects into the mounting block 40 and is aligned with an exterior enlarged diameter flexible hose member 68. In addition, the reservoir 42 communicated with the upwardly extending end section 66 by means of the cross tube 70 to assure proper vacuum relationships within the labyrinth of bended pipes of the viscometer 10.

For visual inspection in the conventional viscometers there has normally been a line that extends around the upwardly extending tube portion 56 at its restricted start point 58 and also a line has been etched or painted in the upwardly extending tube portion 56 at stop point 64.

The new element of the viscometer 10 which forms the subject of this invention resides in the light metering means generally designated 80. Adjacent to and horizontally aligned with the restricted start point 58 of tube section 56 a tube collar or fitting 82 is mounted to the tube 56 by any appropriate means. The fitting 82 includes an inner annular face 83 that interfaces with the tube 56. The fitting can include one half of the circumference of the tube or less. The fitting 82 includes a pair of bores 84 and 85 that extend through the fitting 82 from exterior walls 86 and 87 to the tube 56.

The critical part of the positioning of the bores 84 and 85 is that they be at 90° angles to each other. This illustrated by arrows in FIGS. 3 and 4.

At the stop point 64 of the bulb portion 62 an additional tube collar or fitting 88 is mounted to or formed on the upwardly extending section 56 in the same manner as previously described whereby bores 89 and 91 of fitting 88 are at 90° to each other when the axis extend through the collars 88 to the bore 60 and from an axis that extends through the bores of fitting 88 to the bore 60.

Mounted within each of the bores 84, 85, 89 and 91 are fiber optic rods 90, 92, 94 and 96 respectively. These rods, as can be seen from FIG. 2, extend inwardly into the fittings 82 and 88 and butt against the exterior of the upwardly extending glass portion 56. Each of the fiber optic rods 90 through 96 are bent as shown and extend upwardly into the mounting block 40. With regard to the fiber optic rods 90 and 94 they extend into the block 40 and into a sensing circuit generally designated 114, best seen in FIG. 6. The sensing circuit 114 includes light emitting diode 98 split into two light guides to illuminate and pass down the fiber optic rods 90 and 94 into upwardly extending tube portion 56 at the start point 58 and stop point 64 of the flow of oil to be tested.

The stop fiber optic rods 92 and 96 also extend into the mount 40 and actually pass information back to the sensing circuit 114. Within the mount 40 are two transistors 100 and 102 such as photo-darlington transistors which generally register a high voltage when oil is present.

From the light source which is always on, a lead wire 104 extends to a power source 106. The lead also carries power to the transistors 101 and 102. From the transistors 101 and 102 wires 108 and 110 pass to the trigger logic circuit 18.

For ease of understanding the fiber optic rods 90 and 92 are known as the start detector and the upper fiber optic rods 94 and 96 are known as the stop detectors means. This is more graphically illustrated in FIGS. 3 and 4. In the case of FIG. 4 those rods are shown as the start detector rods and in the case of FIG. 3 those are the stop detector fiber optic rods.

While the fittings 82 and 88 are the preferred form, it should be recognized that individual collars can be utilized to hold the fiber tubes in location against the viscometer tube 56.

At this point the operation of the viscometer is in order. Oil to be tested is poured through the open top 44 into reservoir 42 where it remains at rest and will not pass down through the labyrinth of tubing until such time as it desired. As the light source 98 is always energized a light beam will pass down the respected fiber optic rods 90 and 94 into the upwardly extending glass tube portion 56. As shown by the arrow on the left hand side tube 94 in FIG. 3 the light passes through tube 56 wall onto the capillary wall at 64. In view of the fact that there is air in the tube the angle of internal reflection is about 90°. It would also do the same in rods 90 and 92 if there is no oil present and extend to the right at approximately 90°. If oil is present the angle of internal reflection is greater than 90°. The light reflects off the capillary wall as seen in FIG. 4. The light source will then pass upwardly through the fiber optic rods 92 and 96 respectively to the transistors 100 and 102. At this point when there is no oil the circuit is completed and is closed.

When it is desired for the test to begin it is only necessary to exert a pressure differential on the opening 44 by tapping on the top or with an eye dropper of air into the reservoir 42 and the pressure will cause some oil to flow through the labyrinth of the tubing down the tube portion 52 around the bend 54 and up and commence its upward journey on the upwardly extending tube portion 56. As the oil passes the start point 58 which is the commencement of the enlarged bulb portion 62 the oil no matter what its viscosity or color causes a greater angle of internal reflection and will deflect the light passing from the tube 90° at an angle greater than 90° as illustrated in the arrow on the right hand side of the bore 60 in FIG. 4. At that time the light source is interrupted as it passes to the fiber optic rod 92 which in turn will open the circuit and produce a detectable lesser voltage output from the transistor 100. When this occurs the start time is detected and then as the oil continues to fill the bulb portions 62 it will move upwardly therein to the restricted stop end 64 shown in FIG. 3. When the oil passes the point 64 the light that has been travelling through the fiber optic rod 96 will be redirected. The transistor 102 will then be opened which in turn will issue another signal output of lesser voltage.

Once the oil sample has been tested, then the oil may be purged from the viscometer 10 by introducing a solvent through the tube 68 to clean the tube for the next use in testing. As the construction is such the solvent as poured into the tube 44 will be pulled out of the viscometer due to the vacuum placed at 68.

Turning now to the trigger logic circuitry generally designated 120, this circuitry controls the processing of the outputs from the sensing circuit 114 and particularly transistors 100 and 102.

The circuitry preferably includes quad bilateral switch chip 122 having switches 124 and 126. In additional, there is a quad exclusive OR chip 128 and a Schmitt trigger chip 129 with switch 130.

In operation, the high voltage signal of transistor 100, when the light is undeflected, passes through lead 108 and circuit 120, along lead 138 to switch 124 which is closed until a change. The same is true of transistor 102, where the high signal will pass through lead 110, and switch 126 of circuit 120.

When there is a change in the voltage to a lower voltage at the start of the run when oil deflects the light beam at the start, switch 124 is opened passing on the impulses to the chip 128. When there is a change in the voltage to a lower voltage at the end of the run, the switch 126 is opened with the impulses passing to chip 128.

When the inputs along lines 131 and 133 to the exclusive OR 128 are symmetrically high or low the exclusive OR chip 128 output along line 135 is low. Then the inputs 131 and 133 are assymetrical, that is one is high and one low, as in the case where fluid has just passed 58 and transistor 100 is opened while transistor 102 is closed, the output along line 135 is high. Thus during the run time the exclusive OR output 135 is high.

The signal passing through line 135 is inverted and conditioned in Schmitt trigger 129. The inverted signal via lead 132 and 148 goes to the counter memory circuit 142. It is then used to open a binary counter 150 to a crystal controlled oscillator 152 signal. The counter counts oscillator pulses and stores the total as long as a low signal is on lead 148. The total number of pulses counted directly reflects the flow time. In a simple case the time may be read from the counter through a digital readout 154.

At this point a technician may utilize the readout information to calculate by hand computer or other means the elapsed time in seconds or fraction thereof. From there appropriate calculations may be made to determine the SUS or other viscosity standards desired.

In the event it is desired to utilize a number of viscometers 10 and a number of containers 12 of viscometers 10 in each container 12 then the manual readout discussed above becomes laborious and thus computer science for proper information management, retrieval and print outs are advisable.

Each viscometer 10 is connected to an individual trigger circuit 18 and it's own counter. The counters are scanned via a System Controller Communicator 22 FIG. 1, through address logic 180 as best seen in FIG. 1 or FIG. 8. Data is communicated to the System Controller Communicator 22 and then communicated to the micro computer 32 where final conversion data organization and temporary storage is performed. Data is then transferred along line 28 to a printer or other device.

The invention and its attendant advantages will be understood from the foregoing description and it will be apparent that various changes may be made in the form, construction and arrangements of the parts without departing from the spirit and scope thereof or sacrificing its material advantages, the arrangements hereinbefore described being merely by way of example. We do not wish to be restricted to the specific forms shown or uses mentioned, except as defined in the accompanying claims, wherein various portions have been separated for clarity of reading and not for emphasis.

We claim:

1. A capillary tube viscometer for use in determining viscosity of oil of any clarity flowing between two predetermined points in said viscometer wherein said tube includes a labyrinth of bent glass tube portions including an enlarged upper tube reservoir having an open top a restricted bottom portion moving into a reduced diameter portion a middle tube section, a lower bend portion moving into an upwardly extending tube portion having an upper end and an enlarged testing bulb portion between said lower bend portion and said tube portion, all of said portions and sections having communicating bores forming a continuous flow bore therein, said capillary tube viscometer including:

a mounting block adjacent the open top of said reservoir for receiving and holding said reservoir and for receiving and holding the upper end of said upwardly extending tube section;

said enlarged bulb portion having a bottom start point wherein said bulb portion and said bore of said upwardly extending tube portion communicate and the peripheral wall around said bore is thicker than the diameter of said bore and having an upper stop point wherein said bulb portion and said bore of said upwardly extending end section communicate and the peripheral wall around said bore is thicker than the diameter of said bore;

start light metering means positioned on said tube adjacent said start point adapted to meter said point at one value and yet change the value when said point is interrupted by the flow of oil of any clarity and a light input fiber optic rod extending between said mounting block and said start point receiving light from said light means, a light detector fiber optic rod extending from said block to said start point, and said input fiber optic rod and said light detecting fiber optic rod at said start point are mounted 90° apart;

stop light metering means positioned on said tube adjacent said stop point adapted to meter said point at one value and yet change the value when said point is interrupted by the flow of oil of any clarity and a light input fiber optic rod extending from said block to said stop point receiving light from said light means, a light detector fiber optic rod extending from said block to said stop point, and said light input fiber optic rod and said light detecting fiber optic rod at said start point are mounted 90° apart;

light means in said mounting block connected to said start and stop fiber optic rods;

sensing circuitry mounted in said mounting block associated with said start and stop light metering means adapted to receive the value changes and communicate said changes; and leads from said sensing circuitry adapted to pass the values to appropriate apparatus for calibrating the elapsed time oil moves from the start to stop point to determine viscosity of said oil.

2. A capillary tube viscometer as defined in claim 1 wherein said sensing circuitry includes a transistor for each of said light detector rods of said start and stop points capable of receiving voltage therefrom of a varying value between an unobstructed position and an obstructed position.

3. A capillary tube viscometer as defined in claim 1 wherein said viscometer includes:

a start point fitting on the exterior of said tube, said fitting having a pair of bores on a horizontal plane arranged at 90° to each other;

a stop point fitting on the exterior of said tube, fitting having a pair of bores on a horizontal plane arranged at 90° to each other;

each of said rods having ends that are interfitted within the respective bores with the ends butting said tube viscometer; and said pairs of rods forming a continuous light path by angular reflection of said light in an air glass interface in said tube viscometer to said sensing circuitry of one voltage value, yet capable of emitting another voltage value to said sensing circuitry when oil passes said start or stop point due to a different angle of reflection of light caused by air glass interface as oil of any clarity passing therethrough changes said interface.

4. A capillary tube viscometer as defined in claim 1 wherein there is included:

a bath of heated liquid adopted to receive said tube, said bath to simulate an engine running temperature and create a flow of said oil of any clarity as would take place within an engine;

a sensing circuit including means to furnish light to said light metering means and voltage sensing means to receive back varying voltage from said light metering means dependent upon whether there is oil at either of said start or stop points;

a trigger logic circuit including switching means connected to said sensing circuit to receive the varying voltage and switch various voltage readings to disseminate the same; and a counter memory circuit including a binary counter connected to an oscillator wherein pulsations are received and said pulsations may be read on a digital readout for further calculations into increments of time, whereby the travel time of said oil through said predetermined distance may be determined.

5. A capillary tube viscometer as defined in claim 4 wherein there are a plurality of viscometers submerged in said bath for multiple testing of various oils of any clarity for viscosity and;

a multiple capacity computer is interfaced with said counter memory circuit wherein said readouts may be stored and called upon at random to compute actual time from the pulsations.

* * * * *